United States Patent [19]

Heard

[11] Patent Number: 5,658,281

[45] Date of Patent: Aug. 19, 1997

[54] BIPOLAR ELECTROSURGICAL SCISSORS AND METHOD OF MANUFACTURE

[75] Inventor: David Nichols Heard, Boulder, Colo.

[73] Assignee: Valleylab Inc, Boulder, Colo.

[21] Appl. No.: 566,560

[22] Filed: Dec. 4, 1995

[51] Int. Cl.$^6$ .................................................. A61B 17/36
[52] U.S. Cl. ........................ 606/48; 606/45; 606/41; 606/50
[58] Field of Search ............................ 606/27, 28, 29, 606/37, 39–41, 45, 48–52, 205–208

[56] References Cited

U.S. PATENT DOCUMENTS

| | | | |
|---|---|---|---|
| 4,202,337 | 5/1980 | Hren et al. | 606/48 |
| 4,228,800 | 10/1980 | Degler, Jr. et al. | 606/48 |
| 4,248,231 | 2/1981 | Herczog et al. | 606/48 |
| 4,850,353 | 7/1989 | Stasz et al. | 606/45 |
| 5,324,289 | 6/1994 | Eggers | 606/48 |
| 5,352,222 | 10/1994 | Rydell | 606/37 |
| 5,356,408 | 10/1994 | Rydell | 606/48 |
| 5,484,436 | 1/1996 | Eggers et al. | 606/48 |
| 5,540,685 | 7/1996 | Parins et al. | 606/51 |

*Primary Examiner*—Jennifer Bahr
*Assistant Examiner*—Michael Peffley
*Attorney, Agent, or Firm*—Peter C. Richardson; Lawrence C. Akers; Aaron Passman

[57] ABSTRACT

A bipolar electrosurgical scissors has an improved coagulation capability. Both poles of electrosurgical energy are exposed on the exterior surfaces of each shearing member so that the scissors can be used to coagulate tissue using only one shearing member. There may be two or more electrically conductive regions on the exterior surface of each shearing member. The conductive regions may be formed by laminating, depositing, or inlaying electrically conductive material on the exterior surfaces. The conductive regions are electrically insulated from each other. In one embodiment, the shearing surfaces are also electrically conductive and are each connected to the same electrical pole. In another embodiment, the conductive material that forms one of the conductive regions on each exterior surface also extends through the shearing member to also form a conductive shearing surface.

14 Claims, 3 Drawing Sheets

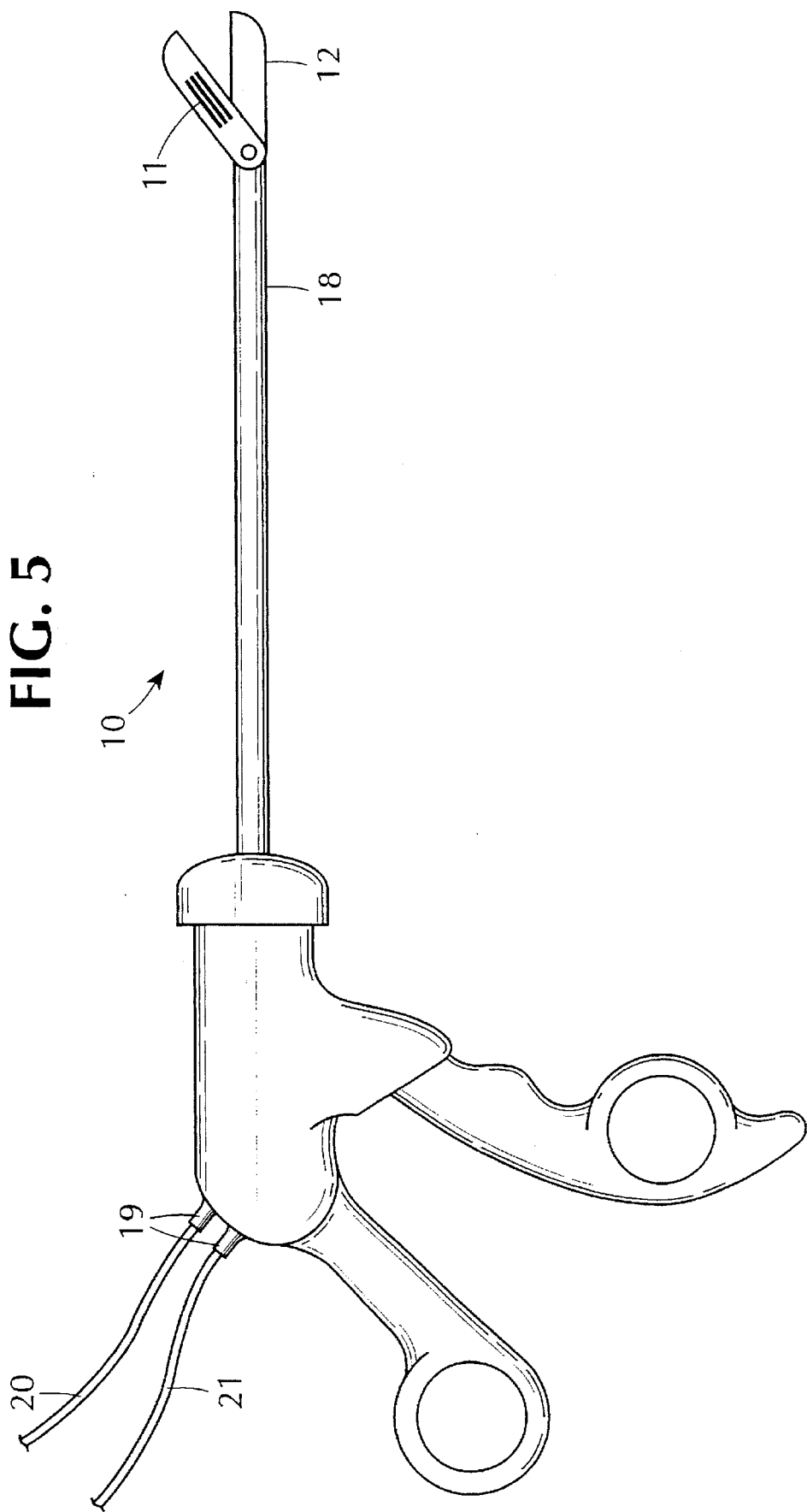

5,658,281

BIPOLAR ELECTROSURGICAL SCISSORS AND METHOD OF MANUFACTURE

FIELD OF THE INVENTION

This invention pertains to surgical scissors which have a bipolar electrosurgical capability, and more particularly to scissors which incorporate two electrical poles on the exterior surfaces of its shearing members in a manner that provides for better tissue coagulation.

BACKGROUND OF THE DISCLOSURE

Electrosurgical tools have been characterized as monopolar or bipolar. Monopolar electrosurgery refers to a configuration where there is a separate return electrode connected to the patient, so that only one electrical pole is carried on the electrosurgical tool. In contrast, bipolar electrosurgery refers to a configuration where both electrical poles are carried on the surgical tool. Monopolar and bipolar electrosurgical tools each offer certain advantages and disadvantages to the surgeon.

One of the advantages of monopolar electrosurgical tools is that the surgeon can apply electrosurgical current whenever the conductive portion of the tool is in electrical contact with the patient. Thus, a surgeon may operate with monopolar electrosurgical tools from many different angles. In contrast, bipolar tools suffer from the drawback that the surgeon must carefully position the tool to ensure that both electrical poles are in electrical contact with the patient in order to apply electrosurgical current. This may limit the range of motion and the angle from which the surgeon can effectively use the bipolar tool.

Surgical shears, or scissors, have been designed for use with electrosurgical energy. The combination of scissors and electrosurgery allows the surgeon to mechanically cut tissue while coagulating the cut tissue using electrosurgical current. As the tissue is cut by the shearing surfaces, the cut tissue slides across the exterior surfaces of the shearing members where it is coagulated. Tissue may also be coagulated while it is being grasped by the scissors and prior to being mechanically cut. The exterior surfaces are the portions of each shearing member which are exposed when the shearing members are in a mated position. The exterior surfaces are generally opposite the shearing surfaces on each shearing member.

There are several variations of electrosurgical pole placement that allow electrosurgical current to flow through the cut tissue. For example, the exterior surface of one shearing member can be energized with a first pole, while the exterior surface of the other shearing member is energized with a second pole. In this configuration, electrosurgical current can flow from one exterior surface, through the cut tissue, to the other exterior surface.

In another example, both exterior surfaces are energized with a first pole, while both shearing surfaces are energized with a second pole. In this configuration, electrosurgical current can flow from each shearing surface, through the cut tissue, to an exterior surface. In both of these examples, it should be observed that each exterior surface is energized with only one electrical pole.

Surgeons often desire to use the scissors to coagulate bleeders without cutting tissue. It would be desirable to perform this function with the shearing members in a closed, or mated, position to avoid exposing the shearing edges. The availability of a coagulation feature on the scissors would avoid the need for a separate coagulation tool. The use of a separate coagulation tool requires the surgeon to switch tools in the middle of a procedure. This can be cumbersome in laparoscopic procedures.

It would be desirable to allow surgeons to use the exterior surfaces of the scissors to coagulate tissue. Presently available scissors have the disadvantage that the exterior surfaces can not be easily manipulated for purposes of coagulation because, as previously described, only one electrical pole is exposed to tissue on each exterior surface. In order to allow current to flow to the tissue, the surgeon must manipulate the scissors to contact both electrical poles to tissue. Thus, both exterior surfaces must be in contact with the tissue, or alternatively, an exterior surface and a shearing surface must contact tissue. These alternatives do not allow the convenience of simply contacting one exterior surface to the bleeding tissue.

U.S. Pat. No. 5,324,289 describes a bipolar surgical shearing instrument. One shearing member carries a first electrical pole, and a second shearing member carries a second electrical pole. At least one shearing surface and edge of the instrument is made from an electrically insulative material. This prevents the shears from creating an electrical short when the two shearing members are in contact. This design suffers from the drawback that only one electrical pole is exposed on each exterior surface. Thus, both shearing members must be in contact with the tissue of the patient in order to apply electrosurgical current.

U.S. Pat. No. 5,352,222 describes an improved bipolar surgical shearing instrument. The shearing surfaces and edges are metallic, thus improving the shearing action of the tool. The shearing surfaces and edges have a layer of electrical insulation which separates them from the electrodes. This design also has only one electrical pole exposed on each exterior surface. As with the previous design, both shearing members must be in electrical contact with the tissue in order to apply electrosurgical current.

SUMMARY OF THE INVENTION

A bipolar electrosurgical scissors is described which will improve the coagulation ability of electrosurgical scissors. In particular, surgeons will find that the bipolar scissors described herein are more easily manipulated for purposes of coagulation while the scissors are in a closed, or mated, configuration. The new arrangement of electrical poles on each shearing member of the scissors will make it possible to hold the tool at many different angles and still provide electrical contact with both of the poles.

There are several embodiments of the improved bipolar scissors. Each embodiment may be applied to a scissors designed for open surgical procedures, or to a scissors designed for laparoscopic surgical procedures. A laparoscopic scissors will have the shearing members attached to the distal end of an elongate support.

In one embodiment, each shearing member may be shaped such that the conductive material which forms the shearing surface also extends through the body of the shearing member to be exposed on its respective exterior surface. This exposes a first electrical pole on the shearing surface as well as on the exterior surface of the shearing member. A second electrical pole is also exposed on the exterior surface of the shearing member. This can be accomplished by embedding or depositing one or more conductive strips next to the first electrical pole on the exterior surface. The first and second electrical poles must be electrically insulated from each other to prevent a short circuit. This arrangement allows the surgeon to coagulate tissue using the exterior surface of either shearing member. The electrosurgical current flows from the first electrical pole, through the tissue of the patient, and then to the second electrical pole.

An alternative embodiment has the conductive regions on the exterior surfaces formed by laminating conductive material onto the scissors shearing members. The shearing members are preferably formed from an electrically insulative material such that the conductive regions will be insulated from each other. A further alternative to laminating the conductive material is to inlay the material or to vapor deposit the material.

BRIEF DESCRIPTION OF THE DRAWINGS

FIG. 5 is a side view of a laparoscopic embodiment of a bipolar electrosurgical scissors.

DETAILED DESCRIPTION OF THE INVENTION

Figure 1:
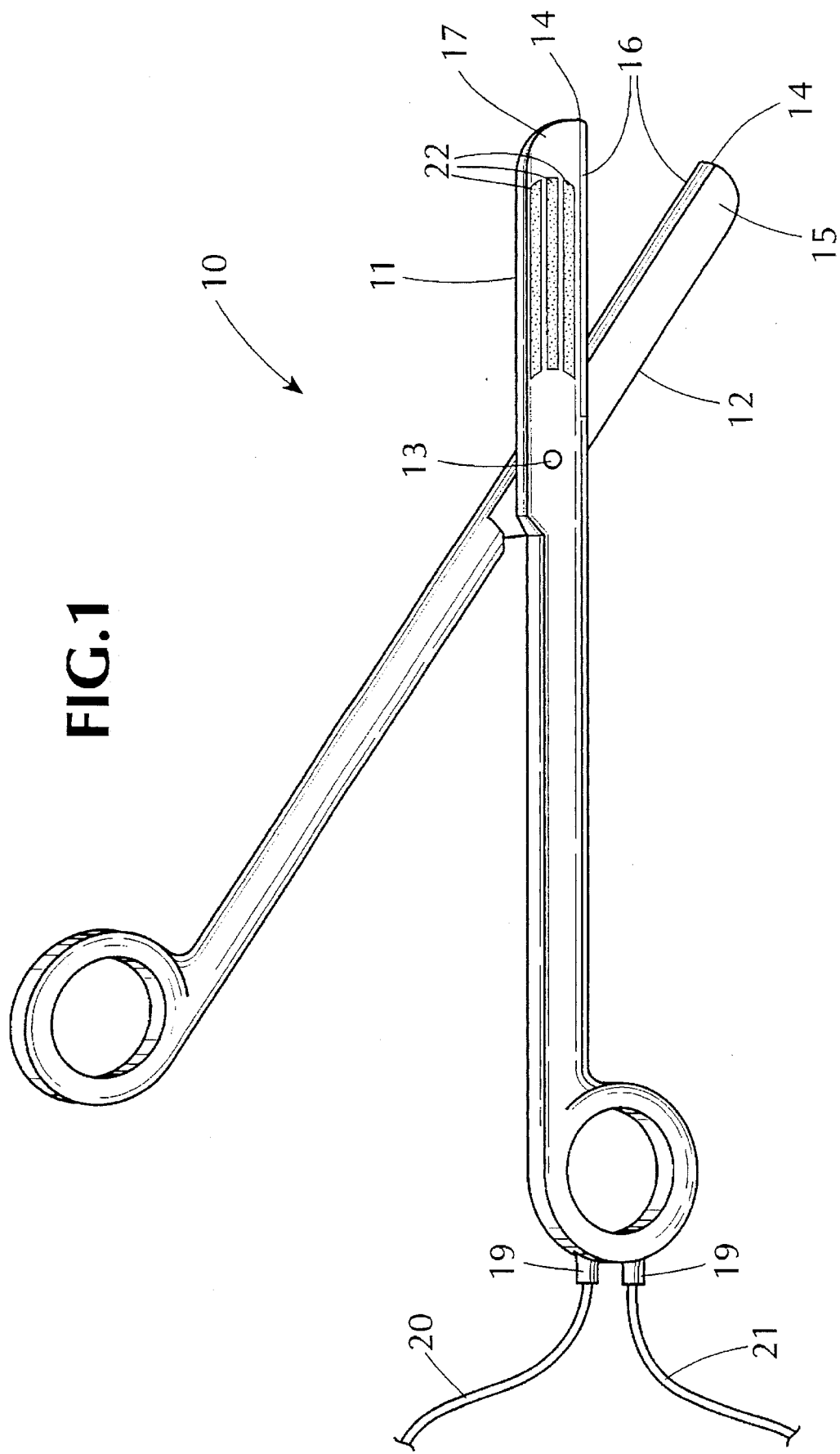
FIG. 1 is a side view of one embodiment of a bipolar electrosurgical scissors.

A bipolar scissors 10 has first and second shearing members 11 and 12, as shown in FIG. 1. The shearing members 11 and 12 are connected by a pivoting joint 13 to allow scissors-like motion of the shearing members 11 and 12. Each shearing member 11 and 12 has a distal end 14 and a shearing surface 15 located between the pivoting joint 13 and the distal end 14. The distal ends 14 of the shearing members 11 and 12 are the ends designed to contact tissue. Each shearing surface 15 is bounded on one side by a cutting edge 16.

Each shearing member 11 and 12 also has an exterior surface 17. The exterior surfaces 17 are the portions of each shearing member 11 and 12 which are exposed when the shearing members 11 and 12 are in a closed, or mated position. The exterior surfaces 17 are generally opposite the shearing surfaces 15 on each shearing member 11 and 12.

In one embodiment, the scissors 10 are designed for laparoscopic surgery. The first and second shearing members 11 and 12 are located at a distal end of an elongate structure 18, as shown in FIG. 5. The elongate structure 18 is designed to fit into a cannula and extend the first and second shearing members 11 and 12 to the operative site of the patient.

Electrical connections 19 are located on the scissors 10 for receiving two poles 20 and 21 of bipolar electrosurgical energy. The electrosurgical energy is high-frequency electrical energy, and thus the two poles 20 and 21 are referenced as a first pole 20 and a second pole 21, respectively. The electrical connections 19 receive the two poles 20 and 21 from an electrosurgical generator. The two poles 20 and 21 are then conducted to different regions on the surgical scissors 10. The arrangement of the different conductive regions 22 makes the bipolar scissors 10 more useful to surgeons than previous designs. In particular, the conductive regions 22 are positioned on the shearing members 11 and 12 such that both poles 20 and 21 are exposed to tissue on each shearing member 11 and 12, even when the scissors 10 are in a closed position.

Figure 2:
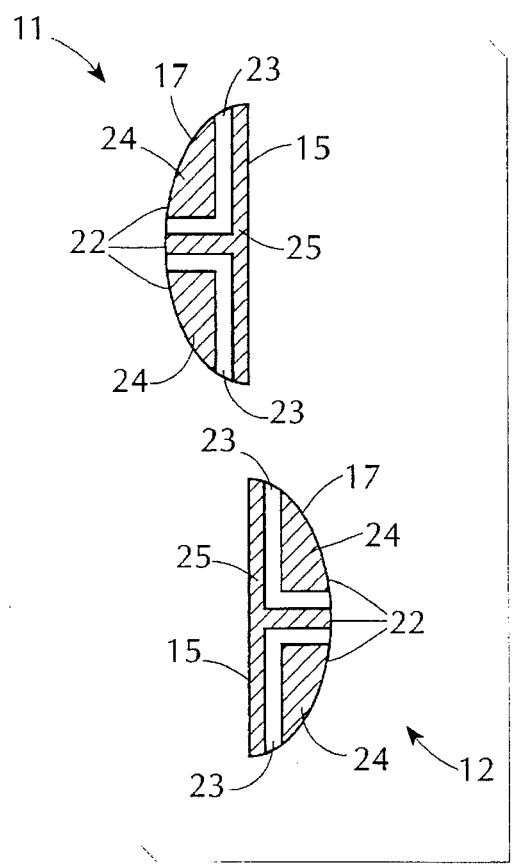
FIG. 2 is a schematic of a front view of a first embodiment of a bipolar electrosurgical scissors.

In one embodiment, the shearing surfaces 15 are each conductive, as shown in FIG. 2. The two shearing surfaces 15 meet during use, and therefore both shearing surfaces 15 are electrically connected to the same pole 20 to avoid an electrical short circuit. In this embodiment, the pivoting joint 13 does not need to be electrically insulated.

Each exterior surface 17 has at least two electrically conductive regions 22 which are insulated from each other. Each pole 20 and 21 is electrically connected to at least one conductive region 22 on each exterior surface 17. This arrangement results in both electrical poles 20 and 21 being exposed on each of the exterior surfaces 17 of the scissors 10. When the surgeon exposes one of the exterior surfaces 17 to tissue, electrical current can flow through the tissue between the conductive regions 17 on that exterior surface 17.

In another embodiment, there are three conductive regions 22 on each exterior surface 17, as shown in FIG. 2. One of the conductive regions 22 on each exterior surface 17 extends through the body of its respective shearing member 11 and 12 to form a conductive region 22 on its respective shearing surface 15. Thus, when the first pole 20 is connected to the shearing surface 15, it is also connected to one of the conductive regions 22 on the exterior surface 17. The other two conductive regions 22 on each exterior surface 17 are electrically connected to the second pole 21.

In the embodiment as shown in FIG. 2, certain conductive regions, each labeled 24 in FIG. 2, on each shearing member 11 and 12, are inlayed in the exterior surfaces 17. An insulative layer 23 separates the conductive regions 22 from each other. The conductive regions 24 are electrically connected to the pole 21. Other conductive regions, labeled 25 in FIG. 2, extend through the shearing members 11 and 12. The conductive regions 25 are electrically connected to expose the pole 20 on both the shearing surfaces 15 and the exterior surfaces 17.

Figure 3:
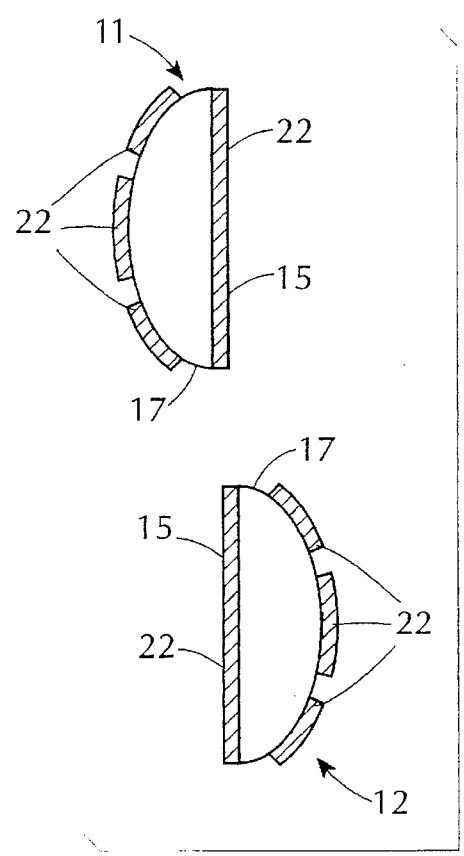
FIG. 3 is a schematic of a front view of a second embodiment of a bipolar electrosurgical scissors.
Figure 3:
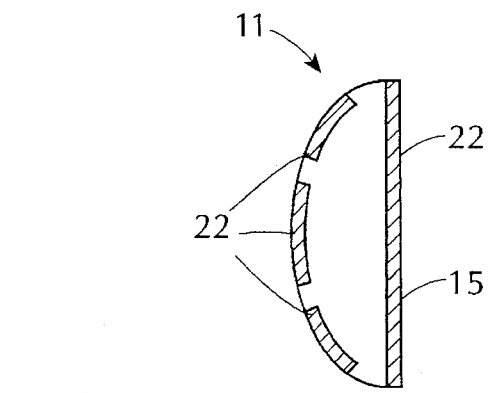
Figure 4:
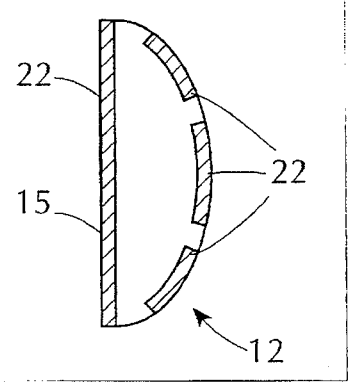
FIG. 4 is a schematic of a front view of a third embodiment of a bipolar electrosurgical scissors.

In the embodiment as shown in FIG. 3, the conductive regions 22 are laminated on the exterior surfaces 17 and the shearing surfaces 15. In an alternative embodiment, also represented by FIG. 3, the conductive regions are vapor or ion deposited on the exterior surfaces 17 and the shearing surfaces 15. In yet another alternative embodiment, as shown in FIG. 4, the conductive regions 22 may be inlayed in the shearing members 11 and 12. The shearing members 11 and 12 in FIG. 4 are constructed of an electrically insulative material.

It is to be understood that the above described arrangements are only illustrative of the application of the principles of the present invention. Numerous modifications and alternative arrangements may be devised by those skilled in the art without departing from the spirit and scope of the present invention. The appended claims are intended to cover such modifications and arrangements.

What is claimed is:

1. A bipolar electrosurgical scissors comprising:

first and second shearing members, each shearing member having a distal end for treatment of tissue;

a pivoting joint connecting the first and second shearing members;

a shearing surface on each shearing member located along the shearing member between the pivoting joint and the respective distal end;

electrical connections on the scissors for receiving two poles of bipolar electrosurgical energy, and an exterior surface on each of the first and second shearing members, each exterior surface located generally opposite its respective shearing surface, each exterior surface having at least two exposed electrically conductive regions which are insulated from each other, wherein each pole is electrically connected to at least one conductive region on each exterior surface.

2. The bipolar scissors of claim 1 wherein the shearing surfaces are electrically conductive and are electrically connected to the same pole such that there is no substantial electrical potential between the shearing surfaces.

3. The bipolar scissors of claim 1 wherein there are three conductive regions on each exterior surface.

4. The bipolar scissors of claim 3 wherein one of the conductive regions on each exterior surface is electrically connected to the same pole as the shearing surfaces.

5. The bipolar scissors of claim 1 wherein one of the conductive regions on each exterior surface extends through its respective shearing member to also form the shearing surface.

6. The bipolar scissors of claim 1 wherein the conductive regions comprise a laminated electrically conductive material on an insulative substrate.

7. The bipolar scissors of claim 1 wherein the conductive regions comprise an inlayed electrically conductive material in an insulative substrate.

8. The bipolar scissors of claim 1 wherein the conductive regions comprise an electrically conductive deposit on an insulative substrate.

9. The bipolar scissors of claim 1 wherein the shearing members are connected to an elongate shaft for insertion through a cannula.

10. A method for constructing bipolar scissors having two shearing members, each shearing member having a shearing surface and an exterior surface located generally on the opposite side thereof, each exterior surface having at least first and second electrically conductive regions which are electrically insulated from each other, the method comprising the steps of:

connecting each shearing surface to a first electrical pole;

connecting the first conductive region on each exterior surface to the first electrical pole, and connecting the second conductive region on each exterior surface to a second electrical pole.

11. The method of claim 10 further comprising the step of forming the conductive regions by laminated electrically conductive material on an insulative substrate.

12. The method of claim 10 further comprising the step of forming the conductive regions by inlaying electrically conductive material in an insulative substrate.

13. The method of claim 10 further comprising the step of forming the conductive regions by depositing electrically conductive material on an insulative substrate.

14. The method of claim 10 further comprising the step of pivoting the shearing members with respect to each other on a conductive pin.

* * * * *